United States Patent [19]
Sullivan et al.

[11] 3,988,469
[45] Oct. 26, 1976

[54] METHOD OF LOWERING PLASMA URIC ACID LEVELS
[75] Inventors: Thomas James Sullivan, Thrussington; Patrick John Kingsley, Loughborough, both of England
[73] Assignee: Fisons Limited, Ipswich, England
[22] Filed: July 1, 1975
[21] Appl. No.: 592,208

[30] Foreign Application Priority Data
July 4, 1974 United Kingdom............... 29602/74

[52] U.S. Cl. ............................................. 424/283
[51] Int. Cl.$^2$......................................... A61K 31/35
[58] Field of Search ................................... 424/283

[56] References Cited
UNITED STATES PATENTS
3,652,765   3/1972   Ellis et al. ............................ 424/283
3,786,071   1/1974   Cairns et al. ........................ 424/283

*Primary Examiner*—Stanley J. Friedman
*Attorney, Agent, or Firm*—Merriam, Marshall, Shapiro & Klose

[57] ABSTRACT

There is described a method for the treatment of hyperuricaemia and/or gout, which comprises administering an effective quantity of 6,8-di-t-butyl-4-oxo-4H-1-benzopyran-2-carboxylic acid, or a pharmaceutically acceptable salt thereof, as active ingredient, to a patient having hyperuricaemia and/or gout. There are also described unit dosage forms of pharmaceutical compositions containing the compound.

10 Claims, No Drawings

METHOD OF LOWERING PLASMA URIC ACID LEVELS

This invention relates to a new method and new dosage forms.

According to our invention we provide a method for the treatment of hyperuricaemia and/or gout, which comprises administering an effective quantity of 6,8-di-t-butyl-4-oxo-4H-1-benzopyran-2-carboxylic acid, or a pharmaceutically acceptable salt thereof, as active ingredient, to a patient having hyperuricaemia and/or gout.

Pharmaceutically acceptable salts which may be mentioned include the ammonium, alkali metal (e.g. sodium, potassium and lithium) and alkaline earth metal salts (e.g. calcium or magnesium), and salts with organic bases, e.g. salts with lower alkylamines such as methylamine or ethylamine, with substituted lower alkylamines, e.g. hydroxy substituted alkylamines or with simple monocyclic nitrogen heterocyclic compounds, e.g. piperidine or morpholine. In particular the sodium salt, or more preferably the free acid, may be used.

The 6,8-di-t-butyl-4-oxo-4H-1-benzopyran-2-carboxylic acid, or the pharmaceutically acceptable salt thereof, may be administered on its own or in combination with a pharmaceutically acceptable adjuvant, diluent or carrier. Examples of suitable adjuvants, diluents or carriers are:- for tablets and dragees; lactose, starch, talc or stearic acid; for capsules, tartaric acid or lactose; for suppositories; natural or hardened oils or waxes. The 6,8-di-t-butyl-4-oxo-4H-1-benzopyran-2-carboxylic acid, or the pharmaceutically acceptable salt thereof, preferably has a particle size of from 0.01 to 10 microns. The compositions may also contain suitable preserving, stabilising and wetting agents, solubilisers, sweetening and colouring agents and flavourings. The compositions may, if desired, be formulated in sustained release form. We prefer compositions which are designed to be administered per os, e.g. to be taken oesophageally and to release their contents in the gastrointestinal tract.

We prefer to use capsules containing the pure drug.

Suitable dosages of the compound are from about 50 to 2,000 mg, preferably 50 to 1,600 mg, per day which may be administered in divided doses from 1 to 6 times a day or in sustained release form. In the initial stages of treatment of acute gout a total daily dosage of from about 400 mg to 1,600 mg given in divided doses from 1 to 4 times a day is generally satisfactory. This dose will in general be administered for up to about 14 days depending on the clinical response, after which time the treatment may be terminated, or, if it is desired to lower the body pool of uric acid, the treatment may be continued at a daily dosage of from about 50 to 400 mg, and preferably from about 50 to 200 mg, preferably given as a single unit daily dose. In the treatment of asymptomatic hyperuricaemia a daily dosage of from about 50 to 400 mg, and preferably from about 50 to 200 mg, preferably given as a single unit daily dose may be used. Thus convenient unit dosage forms comprise from about 50 to 500 mg and preferably 50, 100, 200 or 400 mg of the compound.

The compound may be administered to the patient over a period of from about 1 to about 365 days or longer if necessary.

Specific conditions in which the treatment of the present invention is useful are gout, e.g. acute gout, chronic gout or primary gout; hyperuricaemia associated with leukaemia; hyperuricaemia associated with the commencement of treatment with anti-neoplastic agents; hyperuricaemia associated with treatment with diuretics of the thiazide or similar type, and hypercalciuria.

The method of the invention is also of use in the treatment of pseudo gout, in which the patient has all the symptoms of acute gout, e.g. an inflamed big toe joint, but has a plasma uric acid level which is within normal limits. The method of the invention is also of use in the treatment of patients having raised plasma uric acid levels, but having no clinical symptoms. In such patients the treatment is, in general, designed as a prophylaxis against the onset of clinical symptoms of gout. The treatment of the invention may also, if desired, be used to lower the plasma uric acid level of patients who have normal uric acid levels.

It is believed that the compound of this case does not act as an xanthine oxidase inhibitor.

It is desirable that patients to which the treatment of the invention is applied should have a relatively high fluid intake during the initial stages of the treatment.

The method of the present invention is applicable to a number of mammals, but in particular to humans.

The invention is illustrated, but in no way limited by the following Examples. The human volunteers and patients mentioned in these Examples gave their fully informed consent before the administration of the compound took place.

EXAMPLE 1 a. Nine healthy human volunteers were given 600 mg daily (200 mg t.d.s.) of 6,8-di-t-butyl-4-oxo-4H-1-benzopyran-2-carboxylic acid. Before the treatment the mean uric acid level in the volunteers' plasma was 5.5 mg%, and 24 hours after the last dose it was 2.2 mg%.

b. Three healthy human volunteers were given 900 mg daily (300 mg t.d.s.) of 6,8-di-t-butyl-4-oxo-4H-1-benzopyran-2-carboxylic acid. Before the treatment the mean uric acid level in the volunteers' plasma was 5.5 mg%, and 24 hours after the last dose it was 1.9 mg%.

EXAMPLE 2

The studies of this Example were performed in three parts:

Part I: Two volunteers took either four capsules of placebo (volunteer No 1) or four capsules of 100 mg 6,8-di-t-butyl-4-oxo-4H-1-benzopyran-2-carboxylic acid (i.e. 400 mg 6,8-di-t-butyl-4-oxo-carboxylic acid) (volunteer No 10) as one single morning dose. 10 ml whole blood samples were taken before drug and at hourly intervals after drug for 10 hours, and at 26 hours, the plasma separated off and part stored deep frozen for subsequent 6,8-di-t-butyl-4-oxo-4H-1-benzopyran-2-carboxylic acid analysis.

Part II: Following analysis of the results from Part I, three additional volunteers took 50 mg (volunteer No 4), 100 mg (volunteer No 5), 200 mg (volunteer No 7), and 300 mg (volunteer No 8) of 6,8-di-t-butyl-4-oxo-4H-1-benzopyran-2-carboxylic acid. Blood samples were taken as in Part I.

Part III: To obtain further information on the mode of action of 6,8-di-t-butyl-4-oxo-4H-1-benzopyran-2-carboxylic acid on uric acid handling in the body, four additional volunteers took placebo (volunteers Nos 2 and 3), 100 mg (volunteer No 6) and 300 mg 6,8-di-t-butyl-4-oxo-4H-1-benzopyran-2-carboxylic acid (volunteer No 9). Blood samples were taken as in Part I and at 50 and 74 hours.

All volunteers were on a purine free diet for two days before the experiment. They remained on this diet until the end of the study. On the experimental day they arrived starved and were fed after the four hour blood samples had been obtained. A glass of water was taken at -½, 1½, 3½, 5½, 7½ and 9½ hours. Alcohol was forbidden for 24 hours before and 48 hours after the study.

Table I gives the plasma uric acid levels for all the volunteers.

Table I

Plasma uric acid levels (mg%) in human volunteers taking various doses of 6,8-di-t-butyl-4-oxo-4H-1-benzopyran-2-carboxylic acid

| Time | Vol 1 Plac | Vol 2 Plac | Vol 3 Plac | Vol 4 50mg | Vol 5 100mg | Vol 6 100mg | Vol 7 200mg | Vol 8 300mg | Vol 9 300mg | Vol 10 400mg |
|---|---|---|---|---|---|---|---|---|---|---|
| control | 7.2 | 4.5 | 6.0 | 6.3 | 5.2 | 5.0 | 4.6 | 6.1 | 6.5 | 6.5 |
| 1hr | 6.9 | 4.0 | 6.1 | 6.1 | 5.1 | 5.2 | 4.5 | 6.1 | 6.6 | 6.7 |
| 2hrs | 7.4 | 3.9 | 5.4 | 6.0 | 4.8 | 5.0 | 4.3 | 5.7 | 6.2 | 6.5 |
| 3hrs | 6.9 | 4.6 | 5.8 | 6.0 | 5.0 | 4.3 | 4.2 | 5.6 | 6.1 | 5.9 |
| 4hrs | 7.0 | 4.3 | 5.9 | 5.5 | 4.7 | 4.8 | 4.0 | 5.2 | 6.0 | 5.6 |
| 5hrs | 6.9 | 4.4 | 6.1 | 5.8 | 5.1 | 4.8 | 4.0 | 5.6 | 5.9 | 5.4 |
| 6hrs | 7.3 | 5.0 | 6.6 | 5.6 | 5.3 | 4.8 | 3.8 | 4.9 | 5.3 | 4.2 |
| 7hrs | 7.8 | 5.0 | 6.5 | 5.5 | 5.1 | 4.9 | 3.5 | 4.7 | 5.6 | 5.1 |
| 8hrs | 6.7 | 4.8 | 6.4 | 5.4 | 4.8 | 4.7 | 3.6 | 4.6 | 5.0 | 4.9 |
| 9hrs | 7.0 | 4.9 | 6.3 | 5.6 | 4.8 | 4.8 | 3.7 | 4.9 | 4.8 | 4.6 |
| 10hrs | 6.8 | 4.0 | 6.8 | 5.5 | 5.0 | 4.7 | 3.5 | 4.9 | 4.8 | 4.4 |
| 26hrs | 7.4 | 5.0 | 6.2 | 5.9 | 4.8 | 4.7 | 3.8 | 5.2 | 4.5 | 3.5 |
| 50hrs |  | 4.1 | 5.7 |  |  | 4.9 |  |  | 4.7 |  |
| 74hrs |  | 3.6 | 5.3 |  |  | 4.0 |  |  | 4.9 |  |

EXAMPLE 3

200 mg of 6,8-di-t-butyl-4-oxo-4H-1-benzopyran-2-carboxylic acid were administered orally to a patient suffering considerable pain from gout. One hour after the administration the pain observed subjectively by the patient had decreased considerably. Six to eight hours after the initial administration the patient complained of some return of the pain, which was alleviated for a further eight hours by administration of a second oral 200 mg dose of 6,8-di-t-butyl-4-oxo-4H-1-benzopyran-2-carboxylic acid.

We claim:

1. A method for the treatment of hyperuricaemia or gout, which comprises administering an effective quantity of 6,8-di-t-butyl-4-oxo-4H-1-benzopyran-2-carboxylic acid, or a pharmaceutically acceptable salt thereof, as active ingredients, to a mammal having hyperuricaemia or gout.

2. A method according to claim 1, wherein from 50 to 2,000 mg of active ingredient are administered per day.

3. A method according to claim 2, wherein from 50 to 1,600 mg of active ingredient are administered per day.

4. A method according to claim 3, wherein from 400 to 1,600 mg of active ingredient are administered per day.

5. A method according to claim 1, wherein from 50 to 400 mg of active ingredient are administered per day.

6. A method according to claim 1, wherein the patient has acute gout, chronic gout or pseudo gout.

7. A method according to claim 1, wherein the active ingredient is administered to the patient per os.

8. A method according to claim 7, wherein the active ingredient is administered to the patient oesophageally.

9. A method according to claim 1, wherein the mammal is human.

10. A method of lowering the plasma uric acid level of a mammal having an undesirably high plasma uric acid level, which comprises administration of an effective amount of 6,8-di-t-butyl-4-oxo-4H-1-benzopyran-2-carboxylic acid, or a pharmaceutically acceptable salt thereof to said mammal.

* * * * *